United States Patent
Chott et al.

(10) Patent No.: US 6,302,686 B1
(45) Date of Patent: Oct. 16, 2001

(54) INTEROCCLUSAL DENTAL APPLIANCE AND METHOD

(75) Inventors: Bradley J. Chott; Michael R. Mohrhard, both of St. Louis, MO (US)

(73) Assignee: Keller Laboratories Inc., St. Louis, MO (US)

( * ) Notice: Subject to any disclaimer, the term of this patent is extended or adjusted under 35 U.S.C. 154(b) by 0 days.

(21) Appl. No.: 09/728,547

(22) Filed: Dec. 2, 2000

(51) Int. Cl.$^7$ ............................................. A61C 3/00
(52) U.S. Cl. ........................ 433/6; 128/848; 128/859; 128/602; 128/902
(58) Field of Search .................. 433/6, 215; 128/848, 128/859, 860, 861, 862, 602, 902

(56) References Cited

U.S. PATENT DOCUMENTS

| | | | |
|---|---|---|---|
| 1,818,146 | * 8/1931 | Maker | 128/861 |
| 3,303,844 | * 2/1967 | Johnson et al. | 433/6 |
| 4,955,393 | * 9/1990 | Adell | 128/859 |
| 5,003,994 | * 4/1991 | Cook | 128/848 |
| 5,646,216 | 7/1997 | Watson et al. | |

\* cited by examiner

*Primary Examiner*—Eduardo C. Robert
(74) *Attorney, Agent, or Firm*—Polster, Lieder, Woodruff & Lucchesi, L.C.

(57) ABSTRACT

An interocclusal dental appliance has a liner and an outer shell of a material harder than the liner. The shell extends around the liner through the occlusal surface, the buccal and lingual surfaces, and around an undercut edge of the liner mechanically to secure the harder shell and the liner, but to permit the teeth of the user to engage the liner. The method of producing the appliance includes making a mold of the teeth of a patient forming a liner with cavities complementary to the teeth and occlusal surface, and forming, over the occlusal surface of the liner, over the buccal and lingual surfaces of the liner and around a parimetric edge of the liner a shell of material harder than the liner.

10 Claims, 2 Drawing Sheets

INTEROCCLUSAL DENTAL APPLIANCE AND METHOD

CROSS REFERENCE TO RELATED APPLICATIONS

Statement Regarding Federally Sponsored Research or Development

Not Applicable.

BACKGROUND OF THE INVENTION

This invention has particular application to interocclusal appliances, commonly referred to as splints, for bruxism and temporomandibular joint dysfunction syndrome. However, its utility is not limited to those particular problems.

U.S. Pat. No. 5,646,216, Watson, Jones and Moore, issued Jul. 8, 1997, describes such splints and methods and materials for making them. The disclosures of that patent are incorporated herein by reference.

The present invention is an improvement on the appliances and methods described in the patent, in that in the appliance of this invention, a hard shell covers the exterior occlusal, buccal and lingual surfaces of a relatively soft liner, and covers an outside undercut edge of the liner so as mechanically to join the liner and the shell, but to permit the teeth of the user to engage the soft liner. In the preferred embodiment, the shell and liner are fused at their mutual outer edges by the heat of a bur used in finishing the appliance. The advantages of the appliance of the present invention are, among others, that the joining of the shell and liner are not dependent upon chemical bonding, which in the case of some shell and liner materials is not entirely satisfactory, that the liner can be and is made very thin, to permit the use of a relatively thick shell, which makes for a durable appliance and maintains the integrity of the liner, which is formed initially to fit the teeth of a particular patient.

BRIEF SUMMARY OF THE INVENTION

In accordance with this invention generally stated, a splint is provided in which a liner is molded to a model of a patient's teeth, and a shell harder than the material of the liner is formed over the exterior occlusal, buccal and lingual surfaces of the liner and around an undercut peripheral edge of the liner to produce a mechanical connection between the liner and the shell. The liner and the shell are then fused along mutual peripheral edges of the liner and shell, to reinforce the bond. The shell extends short of the cavities in the liner complementary to the teeth of the user, so as not to interfere with the engagement of the teeth with the relatively soft liner, permitting the soft liner to engage the buccal surfaces of the teeth as well as their lingual and occlusal surfaces.

In the method of this invention, a liner is molded over a model of a patient's teeth in a conventional way. The liner is then reduced, as with an egg-shaped bur, to a thickness of on the order of about 1 mm, over its occlusal, buccal, lingual and outer peripheral edge surfaces, while the liner is supported on its model. The liner is then waxed to the desired dimensions and invested into a flask where the wax is boiled out of the mold, and the shell material is injected into the mold, covering all of the external occlusal, lingual and buccal surfaces of the liner, and extending over the peripheral edge of the liner, but not to the cavities in the liner.

BRIEF DESCRIPTION OF THE SEVERAL VIEWS OF THE DRAWINGS

In the drawings.

Corresponding reference characters indicate corresponding parts throughout the several views of the drawings.

DETAILED DESCRIPTION OF THE PREFERRED EMBODIMENT

Figure 1:
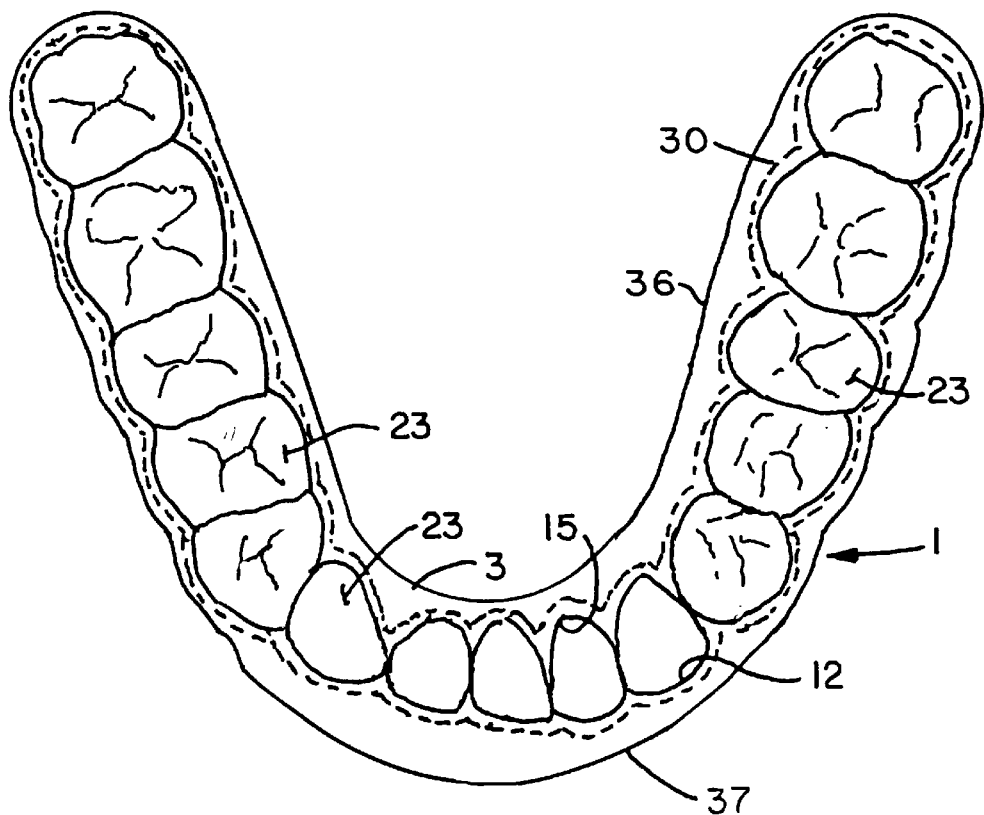
FIG. 1 is a bottom plan view of an appliance of this invention as applied to the bottom teeth of a user, showing toothreceiving cavities in a liner.
Figure 2:
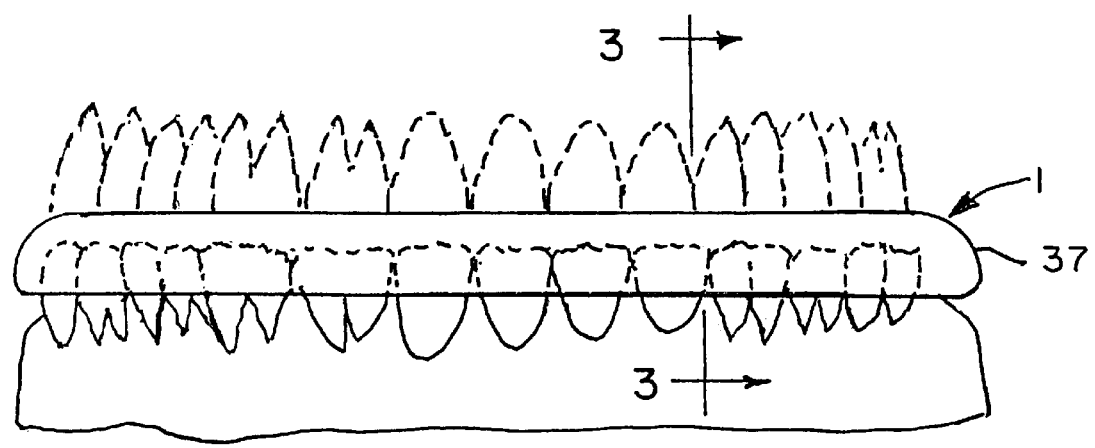
FIG. 2 is a view in side elevation of the appliance in place in the mouth of a user.
Figure 3:
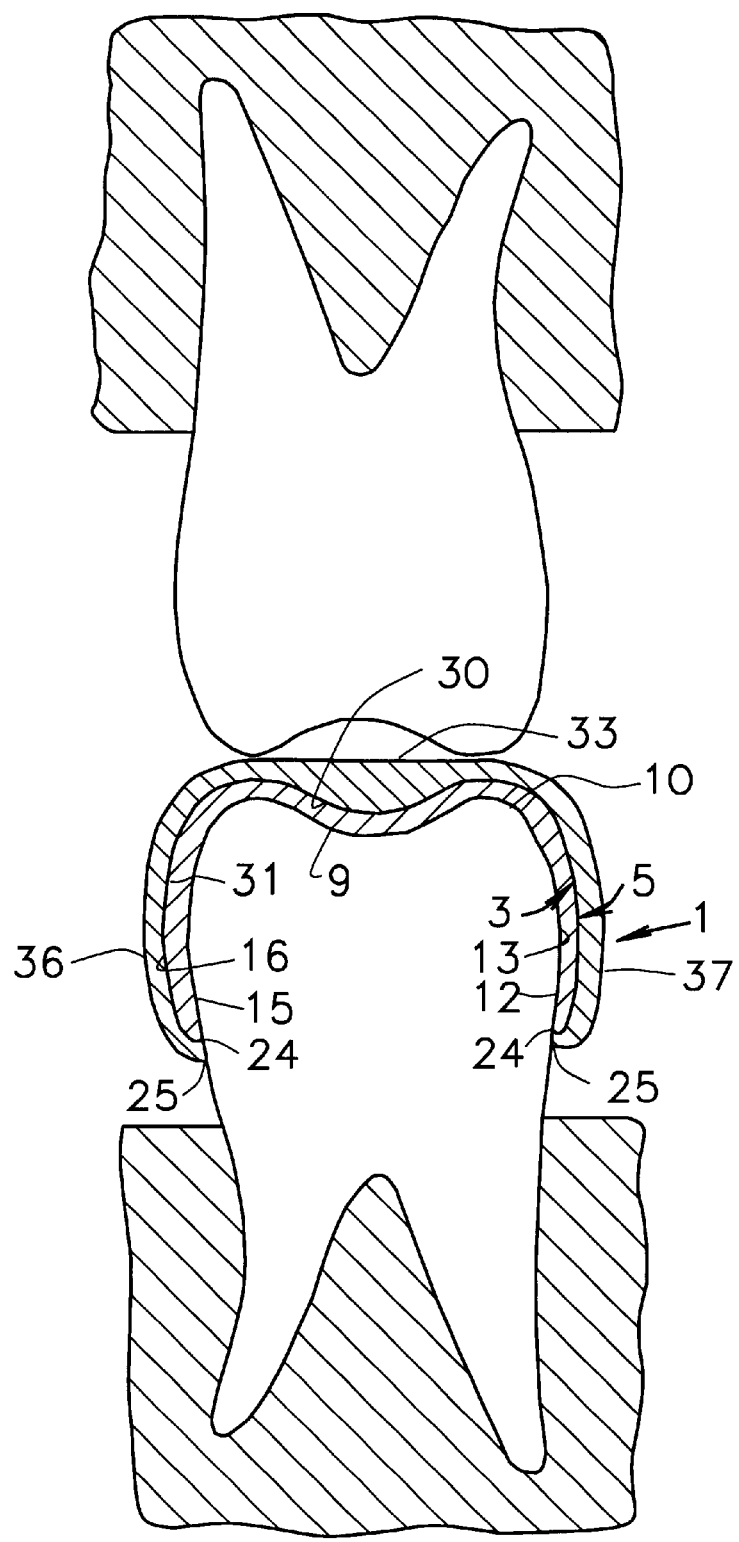
FIG. 3 is a fragmentary sectional view taken along the line 3—3 of FIG. 2.

Referring now to the drawings for one illustrative embodiment of this invention, reference numeral 1 indicates the completed splint, made up of a liner 3 of relatively soft material, and an outer shell 5 of a harder material. The liner 3 is thin, on the order of 1 mm thick. As is explained hereinafter, the liner is formed in the conventional way on a model made from the teeth of the user and then reduced to a thickness on the order of 1 mm. The liner 3 has an interior occlusal surface 9, lingual surface 12, and buccal surface 15. The liner has an exterior occlusal surface 10, lingual surface 13 and buccal surface 16. The liner 3 has in it cavities 23 complementary to the teeth of the user. The liner 3 has a peripheral edge 24. The shell 5 has a peripheral edge 25. The shell also has an inner occlusal surface 30, buccal surface 31 and lingual surface 32, an outer occlusal surface 35, buccal surface 36 and lingual surface 37. The peripheral edge of the shell extends around the peripheral edge of the liner, mechanically binding the liner in the shell. At the peripheral edges, the shell and the liner are fused together.

The liner is made of a relatively soft material, for example a moldable acrylate compound sold under the trademark TALON by Talon Acrylics, Inc. Such material is described in U.S. Pat. No. 5,646,216, column 4 lines 58 through column 5 line 52. The shell is made of a material called Flexite M.P., sold by Rapid Injection Systems Corp. It consists of acrylic polymer and methyl methacrylate monomer. Such materials are described in U.S. Pat. No. 5,646,216, column 4 lines 43 through 48. Both the liner and the shell materials are conventional and well known in this art.

In forming the appliance 1, the liner is first formed conventionally, as explained in U.S. Pat. No. 5,646,216 column 5 lines 62 through column 6 line 13. The liner is then reduced, as by using an egg-shaped bur, to the thickness of 1 mm on all exterior surfaces. On the occlusal surfaces, the cusp tip of the posterior teeth may protrude through the liner and into but not through the shell. This is intentional, to give a stable fit to the appliance when the user bruxes or clinches and allows the splint to retain strength. The liner has been reduced on a model. The model and liner are put on an articulator, and the bite is opened to allow the correct thickness of the shell. The model and the liner are then waxed to dimensions slightly greater than the ultimate size of the shell and invested in an injection flask. The wax is boiled out and the flask heated to keep it warm while the Flexite thermoplastic acrylic is heated. When the acrylic is properly prepared, it is injected into the flask. When the acrylic is set, the splint is removed from the flask and the exterior surface is contoured. This is done with a stone wheel and an egg-shaped bur. When the borders are finished with the stone wheel, the two materials melt together from the heat that the stone creates, sealing them around the borders. The splint is then polished, fitted on the original mold to insure that it is properly formed, disinfected and packaged for delivery.

A full schedule of the procedure is as follows:

1. A working model is produced by a dentist.
2. The undercuts of the working model are surveyed out.
3. The model is duplicated and mounted on an articulator.
4. The duplicated model is waxed to the thickness of 2 mm around the teeth down to the gingival margin on the lingual surface, and three-fourths of the way down on the buccal surface.
5. A mold of the duplicated model is made using hydrocolloid duplicating material; the model is removed from the mold, and the wax boiled off the model.
6. The mold is sprued and vented using a sprue borer and the model is coated with a separator and replaced in the mold.
7. The Talon material is injected into the mold through the sprue mold until the materials is extruded through the vents.
8. The flasks are closed and placed into a pressure pot for 3 hours under 20 pounds of pressure at a temperature of 140°.
9. After the Talon is cured, the liner is finished using an egg-shaped bur to a thickness of 1 mm on all surfaces.
10. The model and the injected liner are then put back on the articulator, and the bite is opened to allow the correct thickness for the Flexite material.
11. The model and the injected liner are then waxed with extensions of the wax to overlap the liner edges.
12. The waxed model and liner are invested in an injection flask.
13. The wax is boiled out and the flask placed under heat lamps to keep the flask warm while the Flexite acrylic is heating.
14. The acrylic is heated to 520° for 26 minutes.
15. The flasks are closed and the acrylic injected into the flask.
16. The splint is then separated from the mold and the exterior surface, contoured.

This is done with a stone wheel and an egg-shaped bur. As the peripheral edges are finished with the stone wheel the two materials melt together from the heat that the stone wheel creates, sealing them around their peripheries.

17. The appliance is polished and then the appliance is fitted on the original mold, to ensure that it fits properly, inspected, and then packaged for delivery.

Numerous variations in the splint of this invention and the method of its manufacture will occur to those skilled in the art in the light of the foregoing disclosure. Merely by way of example, the relative thicknesses of the liner and shell can be varied, although the 1mm thickness of the liner has been found to be eminently satisfactory. The splint can be made for either the upper or lower teeth, or both. The waxes used can be standard base plate waxes. The duplicated model can be waxed down to the gingival margin on the buccal surface or less than all the way to the margin on either of the surfaces. The fusion of the edges can be accomplished with other types of rotating stones. The use of a hot spatula or other metal shape has not been found satisfactory, however, because the heat tends to burn or distort the splint. These variations are merely illustrative.

Having thus described the invention, what is claimed and desired to be secured by Letters Patent is:

1. An interocclusal dental appliance comprising a liner having interior and exterior occlusal, buccal and lingual surfaces and an undercut peripheral edge, and an outer shell of a material harder than the liner, the shell extending around the liner's exterior occlusal, buccal and lingual surfaces and having a peripheral edge extending around said undercut edge of said liner mechanically securing said shell and said liner to one another, said outer shell ending short of cavities in said liner complementary to teeth of a user to permit the teeth of the user to engage said interior surfaces of said liner.

2. The appliance of claim 1 wherein said liner and said hard shell are fused together around their peripheral edges.

3. The appliance of claim 1 wherein the liner has a thickness throughout its extent on the order of 1 millimeter.

4. A method of producing an interocclusal dental appliance comprising making a mold of teeth of a patient; on said mold, forming a liner with cavities complementary to said teeth and with exterior occlusal, lingual and buccal surfaces and an undercut peripheral edge, and thereafter forming, over said exterior surfaces of said liner and around said undercut peripheral edge of said liner but not over said cavities, a shell of material harder than said liner, whereby said shell and liner are mechanically secured together.

5. The method of claim 4 including the additional step of contouring and finishing said shell with a stone bur, and producing with said stone bur sufficient heat around the said peripheral edge to fuse said shell to said liner.

6. The method of claim 4 including the step of reducing the liner overall to a thickness of the order of 1 millimeter before the shell is formed over the liner.

7. The method of claim 6 including the steps of placing the liner, on a model, in an articulator, determining the desired thickness of the shell, waxing the liner and model to the desired thickness, investing the waxed model and liner in a flask, melting out the wax, and injecting into said flask a thermoplastic material harder than the liner to form the shell.

8. The method of claim 6 including the step of contouring and finishing said shell with a stone, and producing with said stone sufficient heat around said peripheral edge to fuse said shell to said liner.

9. A method of producing an interocclusal dental appliance comprising making a mold of teeth of a patient; on said mold, forming a liner with cavities complementary to said teeth and with exterior occlusal, lingual and buccal surfaces and an undercut peripheral edge; forming, over said exterior surfaces of said liner and around said undercut peripheral edge of said liner but not over said cavities, a shell of material harder than said liner and fusing said shell to said liner only around said peripheral edge, maintaining the remainder of the occlusal, lingual and buccal surfaces of said liner unbonded to said shell.

10. An interocclusal dental appliance comprising a liner having interior and exterior occlusal, buccal and lingual surfaces and an undercut peripheral edge, and an outer shell of a material harder than the liner, the outer shell extending around the liner's exterior occlusal, buccal and lingual surfaces and having a peripheral edge extending around said undercut edge of said liner, said peripheral edges of said shell and liner being fused together, said shell and liner being otherwise unbonded to one another, said outer shell ending short of cavities in said liner complementary to teeth of a user to permit the teeth of the user to engage said interior surfaces of said liner.

* * * * *